United States Patent
Smith et al.

(10) Patent No.: US 6,848,444 B2
(45) Date of Patent: Feb. 1, 2005

(54) EMERGENCY LIFE SUPPORT SYSTEM (75) Inventors: Dexter G. Smith, Columbia, MD (US); Protagoras N. Cutchis, Highland, MD (US); William P. Wiesmann, Washington, DC (US); Loland A. Pranger, Montgomery Village, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/920,431

(22) Filed: Jul. 31, 2001

(65) Prior Publication Data

US 2003/0029453 A1 Feb. 13, 2003

Related U.S. Application Data (63) Continuation of application No. 09/401,700, filed on Sep. 23, 1999, now abandoned.
(60) Provisional application No. 60/101,531, filed on Sep. 23, 1998.

(51) Int. Cl.[7] .............................................. A61M 16/00
(52) U.S. Cl. ............................. 128/204.18; 128/204.21
(58) Field of Search .......... 128/204.18, 204.21–204.23, 128/204.28, 205.11, 205.13, 205.18, 205.23, 204.25, 845; 600/21, 22

(56) References Cited

U.S. PATENT DOCUMENTS

| | | | |
|---|---|---|---|
| 3,536,062 A | 10/1970 | Horn ........................... 128/2.05 |
| 3,674,022 A | 7/1972 | Dounoucos ................. 128/142 |
| 3,814,082 A | 6/1974 | Taylor ..................... 128/2.05 R |
| 4,352,991 A * | 10/1982 | Kaufman ..................... 307/9.1 |
| 4,537,190 A | 8/1985 | Caillot et al. .......... 128/204.22 |
| 4,651,731 A | 3/1987 | Vicenzi et al. ......... 128/204.25 |
| 4,860,759 A | 8/1989 | Kahn et al. ................. 128/668 |
| 4,905,688 A | 3/1990 | Vicenzi et al. ......... 128/204.21 |
| 4,972,842 A | 11/1990 | Korten et al. ................ 128/716 |
| 5,002,060 A | 3/1991 | Nedivi ........................ 128/671 |
| 5,188,098 A | 2/1993 | Hoffman et al. ........ 128/204.23 |
| 5,237,987 A | 8/1993 | Anderson et al. ....... 128/204.18 |
| 5,365,922 A | 11/1994 | Raemer .................. 128/204.23 |
| 5,373,842 A * | 12/1994 | Olsson et al. .......... 128/204.21 |
| 5,402,796 A | 4/1995 | Packer et al. ................ 128/719 |
| 5,421,340 A * | 6/1995 | Stanga et al. ................ 600/484 |
| 5,452,714 A | 9/1995 | Anderson et al. ....... 128/205.11 |
| 5,458,137 A | 10/1995 | Axe et al. ............... 128/204.23 |
| 5,494,051 A * | 2/1996 | Schneider, Sr. ................. 5/625 |
| 5,497,766 A * | 3/1996 | Foster et al. ........... 128/200.24 |
| 5,558,086 A * | 9/1996 | Smith et al. ............ 128/204.26 |
| 5,590,648 A * | 1/1997 | Mitchell et al. ............. 600/301 |
| 5,626,151 A | 5/1997 | Linden ........................ 128/897 |
| 5,692,497 A * | 12/1997 | Schnitzer et al. ....... 128/204.21 |
| 5,738,106 A | 4/1998 | Yamamori et al. ........... 128/719 |
| 5,750,077 A | 5/1998 | Schoen ........................ 422/122 |
| 5,868,133 A * | 2/1999 | DeVries et al. ......... 128/204.21 |
| 5,975,081 A * | 11/1999 | Hood et al. .................. 128/845 |
| 5,991,947 A * | 11/1999 | Lavin et al. .................... 5/600 |
| 6,095,138 A * | 8/2000 | Hognelid et al. ....... 128/204.18 |
| 6,230,710 B1 * | 5/2001 | Sobko et al. ................ 128/845 |

(List continued on next page.)

*Primary Examiner*—Henry Bennett
*Assistant Examiner*—Teena Mitchell
(74) *Attorney, Agent, or Firm*—Francis A. Cooch

(57) ABSTRACT

An emergency life support system including a patient ventilator for mechanical breathing assistance; a capnograph to monitor $CO_2$ for ventilation effectiveness; a pulse oximeter for measuring blood stream oxygen saturation; a carbon dioxide sensor; an electrocardiograph (ECG) to monitor cardiac performance; an infusion pump; and alarms and a data recorder. The preferred embodiment uses an oxygen generator to deliver oxygen, to generate electric power to run the ventilation system, and to warm IV fluids and resuscitated air. The generator has electronically controlled valves and a modified valve system that offers the ability to select the oxygen concentration in the air delivered to the patient.

19 Claims, 4 Drawing Sheets

U.S. PATENT DOCUMENTS 6,234,172 B1 * 5/2001 Ausbourne et al. .......... 128/845
6,327,497 B1 * 12/2001 Kirchgeorg et al. ........... 607/3
6,459,933 B1 * 10/2002 Lurie et al. .................... 607/5
6,488,029 B1 * 12/2002 Hood et al. .................. 128/845
6,546,577 B1 * 4/2003 Chinn ............................ 5/600
6,591,135 B2 * 7/2003 Palmer et al. .................. 607/5

* cited by examiner

EMERGENCY LIFE SUPPORT SYSTEM

CROSS REFERENCE TO RELATED APPLICATIONS

This application is a continuation of U.S. application Ser. No. 09/401,700, filed Sep. 23. 1999, now abandoned, which claims priority from U.S. Provisional Application No. 60/101,531, filed Sep. 23, 1998, which is incorporated by reference in its entirety.

STATEMENT OF GOVERNMENTAL INTEREST

This invention was made with Government support under Contract No. DAMD17-97-2-7023 awarded by the Department of the Army. The Government has certain rights in the invention.

BACKGROUND OF THE INVENTION

1. Field of the Invention

The invention relates to critical care medical devices, and, more specifically, to a patient ventilator integrated with state-of-the-art commercial-off-the-shelf (COTS) physiologic sensors and a digitally controlled feedback system for automated monitoring and regulation for use by the first responder to provide on-scene critical life-saving support through more advanced levels of care during the crucial minutes after an injury and during evacuation.

2. Description of the Related Art

Doctrinal shifts that have occurred in the U.S. military since the end of the Cold War place greater reliance on rapidly deployable, mobile, small footprint, advanced medical resuscitation capabilities that can be moved with forces deployed on the battlefield in a time frame consistent with life-saving capabilities. The emphasis is to empower and enhance the combat medic's performance in the early minutes after acute traumatic injury, where medical intervention is most valuable in reversing a potentially fatal condition.

Data, particularly from the American experience in Vietnam, suggests that the largest battlefield mortality rates occur in the prehospital environment where no physicians are present during the early minutes after injury. Furthermore, the data leads to the conclusion that the most effective response to this aspect of the battlefield scenario is to empower medics with technological capabilities that can restore circulation, stem hemorrhage, and maintain an adequate respiratory function and oxygen delivery in acutely injured patients. This coupled with the realization that U.S. forces will be deployed in small units for short-term police actions and battle scenarios, where distances and travel may be extensive, mitigates against rapid removal and transport of heavy, weight-intensive medical equipment and supplies.

While ventilators and/or resuscitators are well known in the art, these devices have been primarily developed for use in hospitals. Thus, such devices are typically fairly cumbersome, utilize the hospital oxygen supply system, and are typically plugged into an alternating current outlet in the hospital. These typical devices are neither self-contained nor portable and, therefore, are unsuitable for battlefield use.

While some portable ventilators have been known in the past, many of these devices typically used bottled oxygen, which has an adverse oxygen supply to weight ratio. In addition, devices which rely on bottled oxygen typically have a relatively short shelf life when compared to devices which rely on chemical oxygen generators.

U.S. Pat. No. 4,651,731 to Vicenzi et at discloses a portable apparatus which is a completely self-contained portable single patient ventilator/resuscitator which utilizes a solid state oxygen generator in the form of a chlorate candle. Several adjustable features and various modes of ventilation are provided on Vicenzi's device and thus the patented apparatus is required to be used by persons with respiratory training. Vicenzi's device uses a pneumatic system to control the valves, and the valving system does not allow for selection between delivery of pure oxygen through to a mixture containing significantly less $O_2$. The oxygen generator is used only to deliver oxygen.

U.S. Pat. No. 4,905,688 to Vicenzi et at discloses a similar portable apparatus which is a completely self-contained portable single patient ventilator/resuscitator which utilizes a solid state oxygen generator in the form of a chlorate candle. Vicenzi's device has less adjustable features and modes of ventilation, thus making it less expensive, less complex, and usable by persons with minimal training. The discussion above relating to U.S. Pat. No. 4,651,731 on the valve system, valve control, and the oxygen generator applies here.

There remains a need for small, lightweight, portable life resuscitation platforms with a long shelf life that can be carried with the troops and used by combat medics. The device must be simple to operate and provide life-sustaining support for the most common battle injuries encountered in modern combat.

More specifically, the unit should support injuries such as respiratory failure and paralysis from tension pneumothorax, hemorrhage, noxis, pulmonary damage due to pulmonary exposures, respiratory inhalation exposures, burn injuries, chemical or biological weapon injuries, and acute ventalthoric control for any other respiratory failure that may occur or be related to sedation, anesthesia or shock. The instrument must be easily resupplied or disposable and all of the capabilities necessary to operate this device must be self-contained within the device. Among these assumed capabilities are suction, monitoring, and ventilatory settings that will permit the medic to operate one device or several devices simultaneously.

Many have attempted to apply technology to the aid station/field hospital arena without a measurable decrease in mortality. The goal of any new device is to be a first rate responder system for the battlefield that will reduce prehospital mortality rates.

SUMMARY OF THE INVENTION

The invention fulfills the above-described need for combat military medical care. The invention brings many of the functions of advanced life support, and can easily be deployed, to casualties at the location of the injury. This provides a vast improvement in care over the "buddy care" system of bandages and IVs currently available.

There is provided according to the invention a self-contained, portable life support system having low susceptibility to electromagnetic interference and being capable of providing autonomous or partially-attended mechanical breathing assistance, monitoring and collection of patient medical data, said life support system comprising;

a. a housing;
b. a low pressure ventilator subsystem comprising:
   i. an interchangeable power supply movably mounted to said housing, said power supply having an input portion and a discharge portion;
   ii. a central processing unit comprising input and output portions, said central processing unit further operatively interconnected to said discharge portion of said power supply;

iii. a switchable exhalation control valve operatively interconnected to said output portion of said central processing unit, said exhalation control valve further operatively interconnected to said discharge portion of said power supply, said exhalation valve further connected to the input end of an exhalation connector;

iv. an adjustable inspiration valve operatively interconnected to said output portion of said central processing unit, said inspiration valve further operatively interconnected to said discharge portion of said power supply, said inspiration valve further operatively connected to the input end of an airflow sensor, said airflow sensor operatively interconnected to said discharge portion of said power supply, said airflow sensor further operatively interconnected to the input end of an inhalation connector, the output end of said airflow sensor further operatively interconnected to said input portion of said central processing unit;

v. a replaceable oxygen supply source, said oxygen supply source connected to the input portion of a patient oxygen mask, said oxygen supply source being capable of providing oxygen and heat output;

vi. a pressure sensor, the input of said pressure sensor connected to the output of said oxygen supply source, said pressure sensor further operatively interconnected to said discharge portion of said power supply, the output of said pressure sensor further operatively interconnected to said input portion of said central processing unit;

vii. an air compressor, said air compressor operatively interconnected to said output of said central processing unit, said air compressor further operatively interconnected to the output portion of said power supply, said air compressor further connected to the output end of said inspiration valve, the output portion of said air compressor further connected to the input end of a suction connector;

viii. a plurality of thermoelectric transducers, said transducers operatively interconnected to said power supply, the input of said thermoelectric transducers operatively interconnected to the output of said oxygen supply source;

c. a sensor subsystem comprising:

i. a capnograph movably mounted to said housing, said capnograph operatively interconnected to said discharge portion of said power supply, said capnograph further operatively interconnected to said input portion of said central processing unit;

ii. a pulse oximeter movably mounted to said housing, said pulse oximeter operatively interconnected to said discharge portion of said power supply, said pulse oximeter further operatively interconnected to said input portion of said central processing unit;

iii. an electrocardiograph movably mounted to said housing, said electrocardiograph operatively interconnected to said discharge portion of said power supply, said electrocardiograph further operatively interconnected to said input portion of said central processing unit;

iv. a carbon dioxide sensor, said sensor operatively interconnected to said discharge portion of said power supply, said carbon dioxide sensor further operatively interconnected to said input portion of said central processing unit;

d. an infusion pump means for delivering fluids to patient, said infusion pump operatively interconnected to said discharge portion of said power supply, said infusion pump further operatively interconnected to said input portion of said central processing unit;

e. at least one alarm, said alarm operatively interconnected to said discharge portion of said power supply, said alarm further operatively interconnected to said output portion of said central processing unit; and f. a continuous data recorder, said data recorder containing input and output portions, said data recorder further operatively interconnected to said discharge portion of said power supply, said data recorder further operatively interconnected to said input portion of said central processing unit, said data recorder being capable of interfacing with an external medical care system and providing said recorded medical data to said external medical care system;

g. a user interface means for setup and monitoring of patient system functions and diagnosis of said ventilator system faults, wherein said user interface is operatively interconnected to said discharge portion of said power supply, said user interface further operatively interconnected to said input portion of said central processing unit.

BRIEF DESCRIPTION OF THE DRAWINGS

FIG. 2, consisting of FIGS. 2A, 2B, 2C and 2D, shows electric power generation using thermoelectric transducers based upon generator-powered ventilation, by use of an oxygen generator, for use in the invention (FIGS. 2A and 2B) and IV fluid warming based upon generator powered ventilation by use of an oxygen generator, for use in the invention (FIGS. 2C and 2D).

DETAILED DESCRIPTION

Aggressive far forward casualty care should reduce the pre-hospital mortality rates experienced by American Forces on the battlefield and shrink the footprint of battlefield medical logistics. Initial improvements must be directed at hemorrhage control and hemostasis. However, ventilatory support following acute respiratory failure secondary to inhalational injury, penetrating thoracic injury, and respiratory paralysis following chemical weapon exposure is mandatory for successful rescue of battle casualties. The invention was designed to operate within the logistical limitations of the forward area and to provide critical life-saving support during the crucial minutes after an injury and during evacuation. The invention can substantially reduce the mortality rate associated with trauma, shock and respiratory compromise due to chemical and biological agents.

Currently, there is no transportable system that can provide acute ventilatory support for combat injuries or chemical or biological weapon paralysis of the ventilatory system that can be delivered in a package and operated by a medic in a time frame that is consistent with the survival of the injured soldier. The invention provides that capability in a very small, controlled, easily operated (specifically designed for first responders) and rugged package and will, most assuredly, contribute to life support and life saving capabilities for the U.S. military.

The invention provides a device including a patient ventilator for mechanical breathing assistance; a capnograph to monitor $CO_2$ for ventilation effectiveness; a pulse oximeter for measuring blood stream oxygen saturations; an electrocardiograph (ECG) to monitor cardiac performance; alarms and a data recorder. A principal advantage of this critical care system is the integration and test of these state-of-the-art COTS physiologic sensor subsystems with a new digitally controlled feedback system. This system permits automated monitoring and regulation of the ventilator's rate and volume to provide optimum care, stabilize the patient and minimize the factors leading to post-traumatic circulatory collapse or hypoxia. The invention is rugged, lightweight, portable, and configurable to a variety of standard military vehicles and transports within standard first responder activities.

The invention is designed for front-line use by field medics but is flexible enough to continue operation during evacuation and at a Mobile Army Surgical Hospital (MASH) or Deployable Medical System/Shelter (DEPMED) unit. The unit has power and data output connectors so that it can use external power and data-handling facilities, if available. In addition, this will allow the transmitter system in the invention to be turned off selectively during stealth operations or helicopter transport, when electromagnetic interference (EMI) problems are more likely. The invention is designed for minimal radiated and conducted EMI as well as having low susceptibility to external EMI.

The medical data and alarm transmissions made by the unit are designed for compatibility with military frequency allocations and bandwidth requirements. In addition, as much as possible within these requirements and within power availability limitations, the unit transmits all data in a high-speed burst model to make location of the injured individual difficult. The unit is also designed to decide autonomously the quantity and format of data transmissions within preset design rules to keep transmissions to a minimum.

To simplify logistics planning, the invention can use existing COTS equipment wherever possible. It is anticipated that the invention will find application in the commercial sector. This dual use will also contribute to the logistics requirements of the system.

This invention is an affordable, advanced critical care system designed to operate within the logistical limitations of the forward area. Several advantages of the present invention include:

1. Adapts to multiple transport and logistical scenarios including Medic transport, armored transport, aviation systems and operates within the constraints imposed for far-forward operations.
2. Is lightweight, self-contained, has a long shelf life and features an autonomous architecture that provides a simple, low-cost, first responder apparatus for initial patient data acquisition. As the system advances, the data gathered by the sensor system will allow digitally controlled optimized care to the patient.
3. Continuously records selected patient data and then provides that data to other medical care systems after the patient is transported to a field hospital or other similar location.
4. Remains self-contained and operational for a minimum of one hour without additional power.
5. Provides a low-power, lightweight ventilator system. The system can provide an integrated controller capable of digitally controlling the pump and ventilator to optimize patient care.
6. Provides an integrated pulse oximeter for measuring oxygen saturation in the blood stream. This data will provide feedback on the effectiveness of ventilation efforts or the patient's own respiration.
7. Integrates a capnograph for measuring the effectiveness of breathing and of endotrachiotube (ETT) placement and avoidance of hyperventilation. The data provides feedback on the effectiveness of ventilation efforts on the patient's own respiration.
8. Integrates an ECG monitoring system for measuring cardiac function.
9. Integrates an infusion pump for the delivery of fluids into the patient to manage the effects of shock.
10. Provides suction capability.
11. Reduces pre-hospital mortality rates by being a first responder system for the battlefield;
12. Provides a rugged device appropriate for use on the battlefield or a civilian disaster scene;
13. Has low electromagnetic emissions and can tolerate a high ambient electric field;
14. Allows closed loop control of ventilation based on measured and derived physiological parameters;
15. Has electronically controlled valves, rather than a unit driven by a pneumatic system;
16. Allows for selection between delivery of pure $O_2$ through to a mixture of 28% $O_2$;
17. Uses the heat generated by the oxygen canister to warm IV fluids and air used in resuscitation from room temperature to 40–60° C.;
18. Uses thermoelectric transducers to convert the heat generated by the oxygen canisters into electric power to operate system devices;
19. Monitors the effectiveness of resuscitation by also sensing carbon dioxide;
20. Includes a communications system that allows the establishment of a piconet capable of allowing the attending medical person to establish short range communications with a number of ventilator units, further allowing the short range remote monitoring of patient and ventilator functions.

Figure 1:
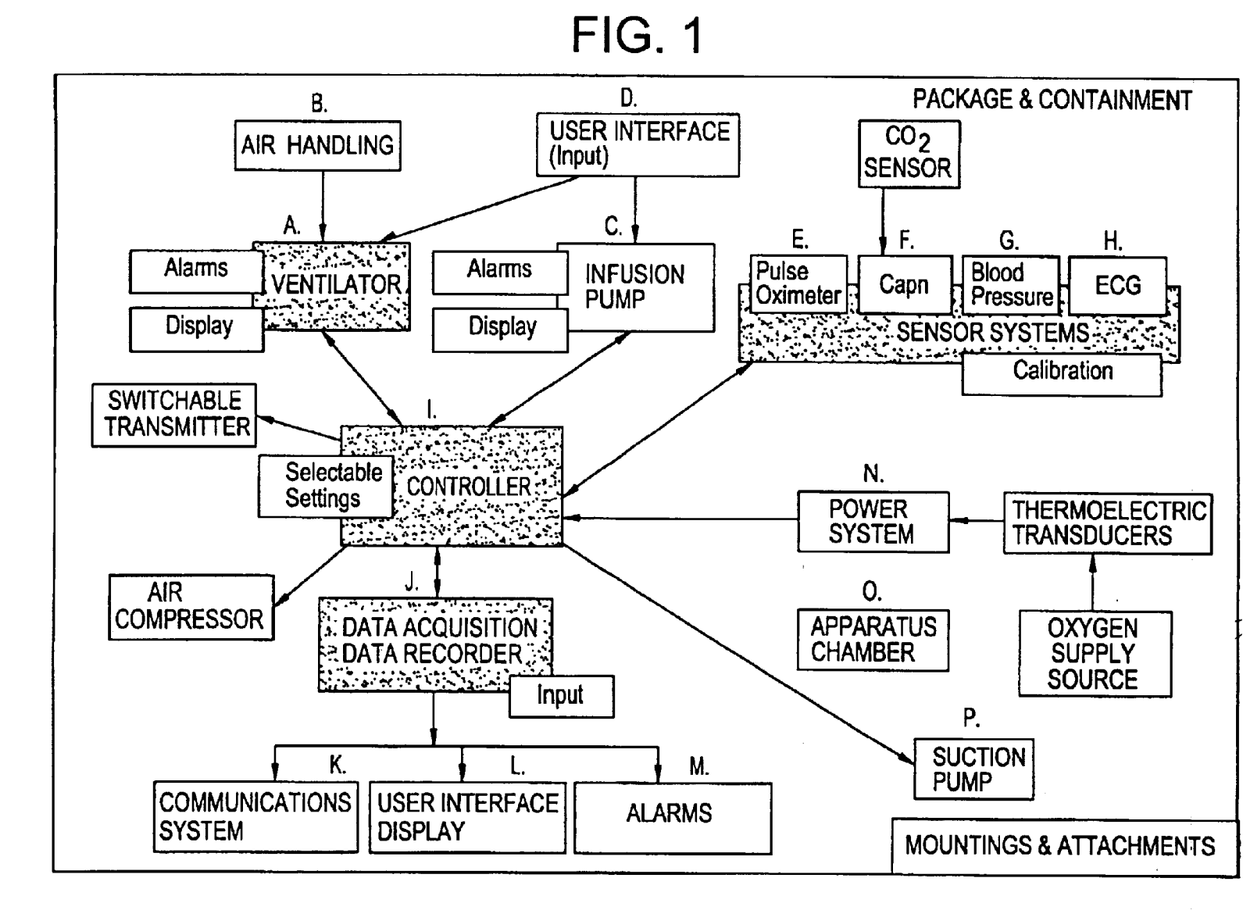
FIG. 1 shows a block diagram of the invention.

The invention is described in more detail with reference to the figures. FIG. 1 is a block diagram of the invention that illustrates how the invention integrates state-of-the-art physiologic sensors with a new digitally controlled feedback system. The invention provides: a patient ventilator (A) for mechanical breathing assistance; an air handling apparatus (B); an infusion pump (C) to deliver fluids into the patient to manage the effects of shock; a user interface (D) for input of parameters; a pulse oximeter (E) for measuring blood stream oxygen saturation; a capnograph (F) to monitor $CO_2$ for ventilation effectiveness; a blood pressure monitor (G); an electrocardiograph (ECG) (H) to monitor cardiac performance; an apparatus controller (I); a data acquisition/data recorder device (J); a communications system module (K); a user interface display module (L); alarms (M); a power systems module (N) for supplying power to the apparatus components; an apparatus chamber (O) for storing additional apparatus components; and a suction pump (P).

The invention is unique in its approach to be a first responder, rugged, portable ventilator unit that will have a measurable effect on mortality statistics on the battlefield or a civilian disaster scene. It is small, lightweight, self-powered, and has an extremely long shelf life. It will have low electromagnetic emissions and can tolerate a high ambient electric field. The sensors combined with on-board controller will allow closed loop control of ventilation based on measured and derived physiological parameters. In one embodiment, an oxygen generator will power the ventilator subsystem and warm system fluids.

The invention is designed to be a compact, stand-alone, self-powered instrument system whose primary function is to provide continuous ventilatory support for a 1-hr. period. Significant characteristics of the invention, as shown in FIG. 1, are:

(A) Ventilator, functional displays and alarm.
(B) Air handling apparatus that includes interconnection of a face mask or intubation device to a replaceable NBC filter.
(C) IV fluids infusion pump with functional display and alarm.
(D) User interface for inputs from external devices, input settings, power, alarm resets, and sensor calibrations.
(E) Pulse oximeter sensor for monitoring oxygen saturation in blood stream.
(F) Capnograph (cpn) sensor for monitoring effectiveness of ventilation in the lungs.
(G) Blood pressure monitor (BP).
(H) Electrocardiogram (ECG) electrodes for monitoring.
(I) Controller to sensor interface.
(J) Data acquisition and recording system that will:
(1) accept user inputs on patient identification, critical signs (e.g., Personal Data Monitor), trauma checklist, patient characteristics;
(2) continuously record patient ventilatory data, sensor data, and freshly logged user inputs; and,
(3) send data and messages to the communications bus, user displays, and alarms.
(K) Communications system that will transmit key patient and instrument status messages to remote locale on command.
(L) User Interface Display for viewing patient status, instrumentation status, and commands received from the casualty coordination.
(M) Alarms system that not only reports instrument dysfunction, but also when patient status is beyond the acceptable bounds a derived from decision aids or external command.
(N) Power systems to instruments, microprocessors, displays, and telemetry.
(O) Apparatus chamber for housekeeping of attachments and spares.
(P) Suction pump.

The ventilator modes should satisfy the largest user community possible without unduly adding to the ventilator size, weight, power requirements, etc. Preliminary findings indicate that an assist control mode is most suitable for battlefield trauma use.

Powering the ventilator of the invention is key. Many civilian ventilators use compressed air as the driving source. The ventilator valves may then be electrically or mechanically controlled. However, military and civilian personnel agree that battlefield use of compressed air cylinders is unacceptable. Power source alternatives included the standard compressor, a high-speed turbine, mechanical bellows or pump, and an oxygen generator.

The preferred embodiment uses an oxygen generator to deliver oxygen, power the ventilator system by reducing the size of batteries needed with attached thermoelectric devices, and warm fluids used by the system.

Figure 2A:
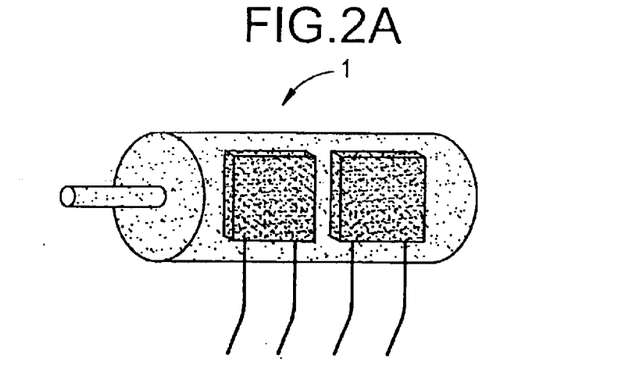
Figure 2B:
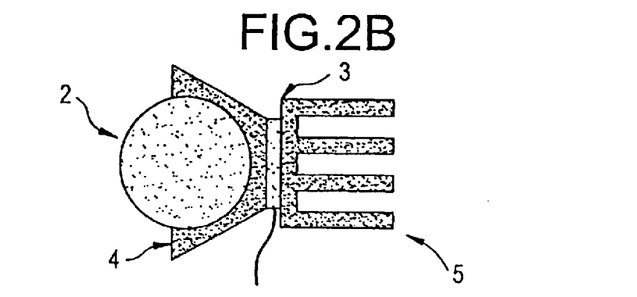
Figure 2C:
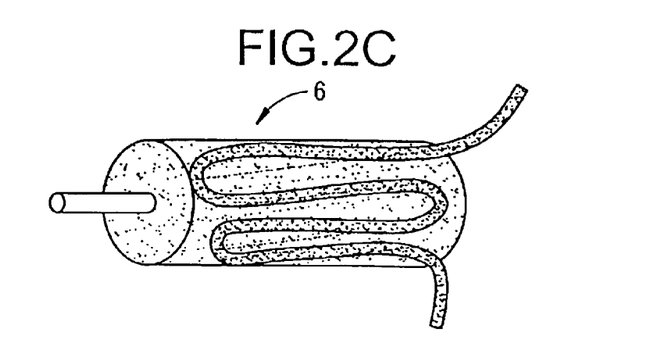
Figure 2D:
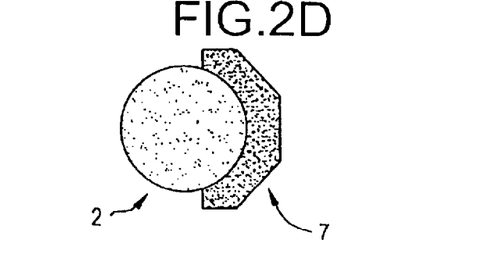

As shown in FIGS. 2A and 2B the oxygen generator (2) can be used to power the ventilator system through the use of thermoelectric devices (3) with the excess heat (slow exothermic chemical reaction) produced by the generator (2). At rest, about 3% of the total power consumption of a human is used for breathing. This works out to about 3 Watts. Simple mechanical ventilation assuming working against 2.3 psi above atmospheric would require about 6.5 Watts. Thus, the ventilator system requires at least half of the available power for the invention. A means for capturing the excess heat is a thermal jacket (4) that attaches to the oxygen generator (2). This thermal jacket (4) delivers heat to the thermoelectric device (3). A heat sink (5) is used on the other side of the thermoelectric device (3) to maintain the proper temperature differential across the thermoelectric device (3). Intravenous (IV) fluids can also be warmed, as shown in FIGS. 2C and 2D, by placing the tubing (6) in contact with the excess heat from the oxygen generator (2). The tubing will be contained in a second thermal jacket (7) that serves to maintain the proper temperature seen by the IV tubing (6).

The excess heat given off by the oxygen generator (2) can also be used to warm IV fluids (6) and resuscitate air through the technique shown in FIGS. 2C and 2D. The oxygen generator (2) output can use electronically controlled valves and have a modified Venturi valving system to allow for selection between delivery of pure $O_2$ (lasting approximately 15 minutes) through to a mixture of 28% $O_2$ (using filtered air from the surrounding environment and lasting approximately one hour using current generator configured canisters.)

Other than the oxygen generator, many other techniques are available for the ventilation system. For example, bellows, air compressors, compressed air and turbine pumps are also possible embodiments for mechanical ventilation. However, these technologies do not all possess the wide range of benefits an oxygen generator provides.

The apparatus is of a size and weight so that it is suitable to be carried by a single person. For example, this lightweight package can be approximately 18 inches wide and 22 inches long and about 6 inches deep.

Figure 3:
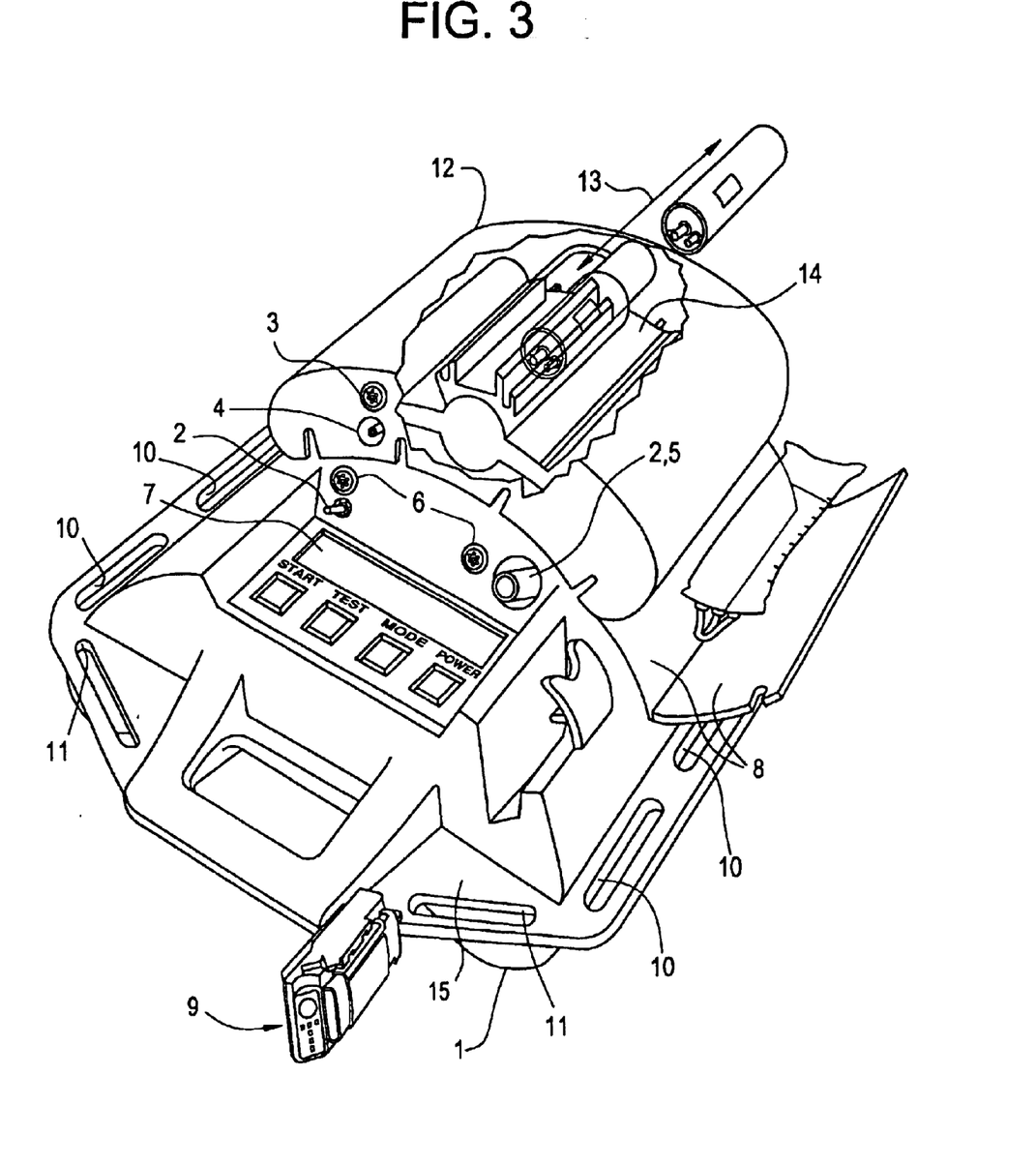
FIG. 3 illustrates a design for an actual unit of the invention.

FIG. 3 illustrates a design for an actual unit of the invention. Included in the design is a curved back support structure (1) that will allow the invention to lie alongside the patient and attach to either an extremity or the chest in order to be co-located as close to the patient as possible. Outlets for the tubing (2), power (3), and oxygen (4), as well as the ventilatory connections (5) and patient monitoring sensors (6) are easily accessible to the patient and to the user.

Only four buttons are required to operate the device: the large alpha-numeric display (7), located on the top of the device, can be viewed easily by the operator. The invention is designed to be constructed from a lightweight, highly durable plastic material and can be produced in any color desired. Recessed panels (8) for IV fluids and the incorporation of an IV pump (9) are conveniently located for operator use and accessibility. Strap attachment ports (10) and slots (11) are provided on each side, permitting the device to be attached to a wall, a transport vehicle, a stretcher or to an ambulance interior.

The detachable oxygen canister pack (12) can be refitted with oxygen generating generators (13) in a plug in-plug out mode during use or the entire pack can be replaced. Alternatively, if the invention is operated by supplemental oxygen and gas, this oxygen generator pack (13) can be removed and the device can operate with a smaller footprint. Within the power oxygen heater module (14) is a site to attach the IV tubing. This design takes advantage of the heat produced by the oxygen generators and enables IV fluid to be warmed as it is infused into the patient.

The entire unit (15) is designed to be hermetically sealed and to operate while wet, or even partially submerged. Slight modifications in the design shown in FIG. 3, including changes in positioning the operating dials, the alphanumeric display, the patient ventilator and monitoring outputs, and the actual placement of the oxygen generating generators on the device may be appropriate in order to more seamlessly integrate the subsystems and/or for manufacturing considerations.

A mockup of the ventilator subsystem of the invention has been fabricated. Off-the-shelf devices such as the ECG and pulse oximeter were not part of the mockup because their dimensions and functionality are well known. Although specific examples of off-the-shelf devices are mentioned herein, such representative examples are for illustrative purposes only and the final embodiments of the invention are intended to include equivalent components available from a variety of manufacturers.

The design goal was to build a mockup that could ventilate for one half hour to an hour using internal battery power. Further goals were that the unit be made as small as possible and use the same or similar components to those that would be in the final invention prototype. To keep the size and complexity of the first prototype down either oxygen generators or associated thermoelectric generators were incorporated. Lastly, it was a design goal to explore software features into the prototype that would demonstrate features and control algorithms either directly or indirectly applicable to the final unit.

Figure 4:
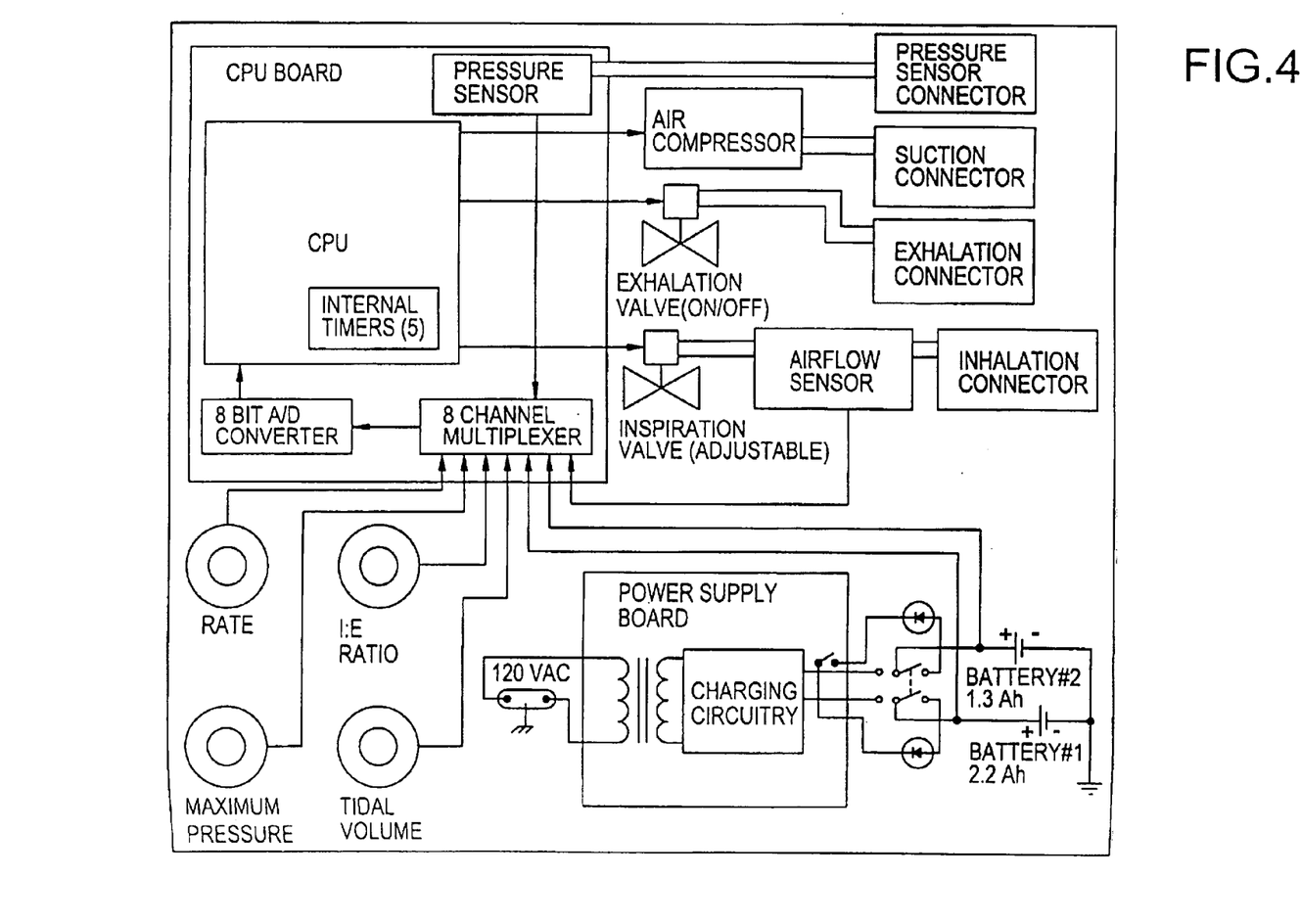
FIG. 4 shows a block diagram of the ventilator subsystem of the invention.

FIG. 4 is a block diagram that shows an exemplary hardware configuration. The mockup system design centers around a compressor, several control valves, a power supply board, and a processor board based on a Motorola 68HC811 microprocessor. The four front panel adjustable parameters are the tidal volume (200 to 620 cc in 10-cc increments), respiratory rate (8 to 20 per minute), I:E ratio (1:1 to 1:3.0 in steps of 1:0.1), and maximum inhalation pressure (10 to 40 mm Hg in steps of 1-mm Hg). The maximum pressure is also determined by an adjustable pop-off valve in the exhalation circuit.

The adjustable parameters are set as 0 to 5-V voltage levels through front panel mounted potentiometers. An 8-bit A/D digitizes the voltage and the software adjusts each to the appropriate value for that parameter. All values are displayed on the Liquid Crystal Display (LCD) during operation. A front panel LOCK/UNLOCK switch prohibits the processor from reading the settings so that accidental adjustment is difficult. The processor also monitors the voltage of both batteries and switches in the second when the voltage of the first drops below a preset value. Circuitry on the processor board also implements an 8-bit D/A converter that generates 2.2 to 10.2V for the adjustable valve.

The power supply board contains two constant-current, voltage-limited chargers for the two lead-acid batteries. A front panel switch selects whether the FFCCU is in battery charge mode or usage mode. Both batteries charge simultaneously. Although there is a switch on the front panel of the mockup to allow direct 120-VAC operation, the 3-amp regulators and some other circuitry required to operate in this mode were not added. They could be easily added at a later time.

The air compressor selected is a Thomas G/07-30 W that produces 14.5 LPM at 0 psi and 4.6 LPM at 10 psi. The normal operating pressure should be about 1 psi above atmospheric. This unit is specified to draw 3.1 amps at 12V but bench measurements showed 2.7 to be a more accurate value. This compressor was chosen for its relatively lightweight and small size (5.9" long, 1.93" in diameter, and weighs 1.46 lb). This unit will not ventilate a human without the additional oxygen generators; however, for mockup purposes, it will suffice. A number of slightly larger compressor units are available for the final version of the invention.

The air-flow sensor is a Honeywell Model AWM5104VN (calibrated at the factory with nitrogen). This unit outputs a very linear 1.0 to 5.0V over a flow range of 0 to 20 LPM. It is quite large (6.4" from end to end) but was selected because it has low impedance flow that eases the energy requirements of the compressor and is currently in a ventilator product from Oceanic Medical.

The pressure sensor is a Motorola MPX2010GP that has a range of 0 to 1.45 psi and outputs 25 mV full scale. It is located on the processor control board and is connected through internal and external tubing to a point right at the endotracheal tube connection in the patient "Y" circuit so as to measure the actual ventilating pressure without the flow induced drops in the rest of the system. This sensor goes through a 3-op-amp differential instrumentation amplifier to obtain voltages usable to the A/D converter.

The air flow control valve is a Teknocraft Inc. Model 202611 adjustable valve. The exhalation valve, which only implements an ON/OFF function is a model 22R9DGM from Peter Paul Electronics.

The batteries chosen for the prototype are Panasonic 12 V lead acid cells with 2.2 and 1.3 Ah capacities. Two batteries were chosen so that the feature of the system that allows voltage checking and automatic battery switch over to occur could be implemented and tested. If this feature is implemented in the final version of the invention, it should be accompanied by a radio link warning to the medic that the system is on its reserve battery with approximately 15 to 20 minutes of reserve operation remaining.

The ventilator subsystem mockup weighs 13.4 lb (without the case). The batteries described above weigh 2.6 pounds. Each of the three oxygen generators weighs 2.5 lb for a combined total weight of 7.5 pounds. Currently, the system total weight is 23.5 lb, with only 1.5 lb available for the case, and all off the shelf physiologic sensors.

The mockup filled the need to assemble the pieces necessary for the ventilator subsystem, but was not built to address the need for minimum weight. Thirty, convenient to obtain, brass fittings were used to simplify the plumbing in the mockup which added significant weight. Also, the two (off the shelf) low pressure valves weighed a total of 3 lb. Thus, there are significant weight savings available using this mockup as the starting point.

It will be understood that the above described embodiments of the present invention are susceptible to various modifications, changes, and adaptations, and the same are intended to be comprehended within the meaning and range of equivalents of the appended claims. Further, although a number of equivalent components may have been mentioned herein which could be used in place of the components illustrated and described with reference to the described embodiment, this is not meant to be an exhaustive treatment of all the possible equivalents, nor to limit the invention defined by the claims to any particular equivalent or combination thereof. A person skilled in the art would realize that there may be other equivalent components presently known, or to be developed, which could be used within the spirit and scope of the invention defined by the claims.

What is claimed is:

1. A self-contained, portable life support system having low susceptibility to electromagnetic interference and being capable of providing autonomous or partially-attended mechanical breathing assistance, monitoring and collection of patient medical data, said life support system comprising;

a. a housing having dimensions no greater than two feet by two feet by one foot;
b. a low pressure ventilator subsystem comprising:
   i. an interchangeable power supply movably mounted to said housing, said power supply having an input portion and a discharge portion;
   ii. a central processing unit comprising input and output portions, said central processing unit further operatively interconnected to said discharge portion of said power supply;
   iii. a switchable exhalation control valve operatively interconnected to said output portion of said central processing unit, said exhalation control valve further operatively interconnected to said discharge portion of said power supply, said exhalation valve further connected to the input end of an exhalation connector;
   iv. an adjustable inspiration valve operatively interconnected to said output portion of said central processing unit, said inspiration valve further operatively interconnected to said discharge portion of said power supply, said inspiration valve further operatively connected to the input end of an airflow sensor, said airflow sensor operatively interconnected to said discharge portion of said power supply, said airflow sensor further operatively interconnected to the input end of an inhalation connector, the output end of said airflow sensor further operatively interconnected to said input portion of said central processing unit;
   v. a replaceable oxygen supply source, said oxygen supply source connected to the input portion of a patient oxygen mask, said oxygen supply source being capable of providing oxygen and heat output;
   vi. a pressure sensor, the input of said pressure sensor connected to the output of said oxygen supply source, said pressure sensor further operatively interconnected to said discharge portion of said power supply, the output of said pressure sensor further operatively interconnected to said input portion of said central processing unit;
   vii. an air compressor, said air compressor operatively interconnected to said output of said central processing unit, said air compressor further operatively interconnected to the output portion of said power supply, said air compressor further connected to the output end of said inspiration valve, the output portion of said air compressor further connected to the input end of a suction connector;
   viii. a plurality of thermoelectric transducers, said transducers operatively interconnected to said power supply, an input of said thermoelectric transducers operatively interconnected to an output of said oxygen supply source;
c. a sensor subsystem comprising:
   i. a capnograph movably mounted to said housing, said capnograph operatively interconnected to said discharge portion of said power supply, said capnograph further operatively interconnected to said input portion of said central processing unit;
   ii. a pulse oximeter movably mounted to said housing, said pulse oximeter operatively interconnected to said discharge portion of said power supply, said pulse oximeter further operatively interconnected to said input portion of said central processing unit;
   iii. an electrocardiograph movably mounted to said housing, said electrocardiograph operatively interconnected to said discharge portion of said power supply, said electrocardiograph further operatively interconnected to said input portion of said central processing unit;
   iv. a carbon dioxide sensor, said sensor operatively interconnected to said discharge portion of said power supply, said carbon dioxide sensor further operatively interconnected to said input portion of said central processing unit;
d. an infusion pump means for delivering fluids to patient, said infusion pump operatively interconnected to said discharge portion of said power supply, said infusion pump further operatively interconnected to said input portion of said central processing unit;
e. at least one alarm, said alarm operatively interconnected to said discharge portion of said power supply, said alarm further operatively interconnected to said output portion of said central processing unit;
f. a continuous data recorder, said data recorder containing input and output portions, said data recorder further operatively interconnected to said discharge portion of said power supply, said data recorder further operatively interconnected to said input portion of said central processing unit, said data recorder being capable of interfacing with an external medical care system and providing said recorded medical data to said external medical care system; and
g. a user interface means for setup and monitoring of patient system functions and diagnosis of said ventilator system faults, wherein said user interface is operatively interconnected to said discharge portion of said power supply, said user interface further operatively interconnected to said input portion of said central processing unit;

whereby the life support system can be hand-carried by a single person to the patient to be treated.

2. A life support system according to claim 1, wherein said inspiration valve is adjustably capable of delivering between 28–100% oxygen.

3. A life support system according to claim 1, wherein said housing comprises a curved support structure.

4. A life support system according to claim 1, wherein said housing comprises a curved support structure means for attaching said housing to or lying alongside of a patient.

5. A life support system according to claim 1, wherein said housing further comprises a plurality of lateral strap attachment ports and slots.

6. A life support system according to claim 1, wherein said housing further comprises a plurality of recessed panels for attaching fluid reservoirs.

7. A life support system according to claim 1, wherein said housing further comprises a plurality of recessed panels means for attaching fluid reservoirs.

8. A life support system according to claim 1, wherein said power supply comprises at least one battery.

9. A life support system according to claim 1, wherein said power supply comprises an external power source and optionally contains power output and input connectors.

10. A life support system according to claim 1, wherein said power supply contains power output and input connectors means for selectively switching said power supply to an external power source.

11. A life support system according to claim 1, further comprising a switchable transmitter capable of high-burst data transmission, said transmitter being capable of transmitting data in variable quantities and variable formats.

12. A life support system according to claim 1, said ventilator subsystem containing data output connectors, said data output connectors operatively connected to said output portion of said data recorder.

13. A life support system according to claim 1, said ventilator subsystem containing data output connectors means for interfacing with external data-handling facilities.

14. A life support system according to claim 1, wherein said oxygen supply source is operatively interconnected to said output of said thermoelectric transducers, said oxygen supply source being further capable of supplying power via said thermoelectric transducers to said input portion of said power supply.

15. A life support system according to claim 1, wherein said oxygen supply source generates heat for warming fluids and air used in patient resuscitation.

16. A life support system according to claim 1, said ventilator subsystem further comprising an infusion pump, said pump operatively interconnected to said discharge portion of said power supply.

17. A life support system according to claim 1, said ventilator subsystem further comprising an infusion pump means for delivering fluids to patient, said pump operatively interconnected to said discharge portion of said power supply.

18. A life support system according to claim 1, wherein said oxygen supply source optionally is selected from one or more of the following:

a bellows;

an air compressor; and at least one compressed air turbine pump.

19. A life support system according to claim 1, wherein said ventilator subsystem is capable of providing continuous ventilatory support for at least one hour.

* * * * *